US009011406B2

(12) United States Patent
Torigoshi et al.

(10) Patent No.: US 9,011,406 B2
(45) Date of Patent: Apr. 21, 2015

(54) UNDERPANTS TYPE DISPOSABLE DIAPER

(75) Inventors: Keiji Torigoshi, Shikokuchuo (JP);
Kosuke Murai, Shikokuchuo (JP);
Yosuke Mori, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 1011 days.

(21) Appl. No.: 12/309,802

(22) PCT Filed: Jul. 31, 2007

(86) PCT No.: PCT/JP2007/064924
§ 371 (c)(1),
(2), (4) Date: Jan. 30, 2009

(87) PCT Pub. No.: WO2008/016020
PCT Pub. Date: Feb. 7, 2008

(65) Prior Publication Data
US 2009/0198207 A1  Aug. 6, 2009

(30) Foreign Application Priority Data

Jul. 31, 2006 (JP) ................................ 2006-209229
Nov. 30, 2006 (JP) ................................ 2006-324860

(51) Int. Cl.
| A61F 13/58 | (2006.01) |
| A61F 13/62 | (2006.01) |
| A61F 13/56 | (2006.01) |
| A61F 13/493 | (2006.01) |
| A61F 13/496 | (2006.01) |
| A61F 13/49 | (2006.01) |

(52) U.S. Cl.
CPC .............. *A61F 13/56* (2013.01); *A61F 13/493* (2013.01); *A61F 13/496* (2013.01); *A61F 13/5622* (2013.01); *A61F 2013/49087* (2013.01); *A61F 2013/5677* (2013.01)

(58) Field of Classification Search
CPC ............... A61F 2013/49087; A61F 2013/5677
USPC .................................................. 604/389–391
See application file for complete search history.

(56) References Cited

U.S. PATENT DOCUMENTS

| 2,931,747 | A | * | 4/1960 | Dexter | ............................. 428/57 |
| 3,800,796 | A | * | 4/1974 | Jacob | ............................ 604/390 |
| 4,081,301 | A | * | 3/1978 | Buell | ............................ 156/164 |
| 4,555,244 | A | * | 11/1985 | Buell | ............................ 604/392 |
| 4,617,022 | A | * | 10/1986 | Pigneul et al. | ................ 604/391 |
| 4,639,949 | A | * | 2/1987 | Ales et al. | ......................... 2/400 |
| 4,743,239 | A | * | 5/1988 | Cole | ........................ 604/385.23 |

(Continued)

FOREIGN PATENT DOCUMENTS

| DE | 198 13 334 A | 9/1999 |
| GB | 2 267 024 A | 11/1993 |

(Continued)

*Primary Examiner* — Melanie Hand
*Assistant Examiner* — Paula L Craig
(74) *Attorney, Agent, or Firm* — DLA Piper LLP (US)

(57) ABSTRACT

A disposable diaper which can be used both as a tape-fastening type and an underpants type by joining the both side portions of the front body part and back body part respectively to thereby form joined portions on both sides along with a waist opening and a pair of right and left leg openings and in this diaper, perforated lines are formed on the both side portions of the front body part so as to extend from an edge of the waist opening to edges of the leg openings and at least one pair of fastening tapes having hook members on inner surfaces thereof and straddle the perforated lines.

7 Claims, 18 Drawing Sheets

(56) References Cited

U.S. PATENT DOCUMENTS

| | | | |
|---|---|---|---|
| 4,909,804 A * | 3/1990 | Douglas, Sr. | 604/385.29 |
| 4,943,340 A * | 7/1990 | Ujimoto et al. | 156/496 |
| 5,304,162 A * | 4/1994 | Kuen | 604/391 |
| 5,374,262 A * | 12/1994 | Keuhn et al. | 604/391 |
| 5,624,420 A * | 4/1997 | Bridges et al. | 604/365 |
| 5,693,038 A * | 12/1997 | Suzuki et al. | 604/385.23 |
| 5,776,123 A * | 7/1998 | Goerg et al. | 604/391 |
| 6,508,797 B1 * | 1/2003 | Pozniak et al. | 604/385.11 |
| 6,524,293 B1 * | 2/2003 | Elsberg et al. | 604/385.13 |
| 6,579,275 B1 * | 6/2003 | Pozniak et al. | 604/390 |
| 6,972,012 B1 * | 12/2005 | Pozniak et al. | 604/386 |
| 2001/0049516 A1 * | 12/2001 | Shimada et al. | 604/385.11 |
| 2002/0045879 A1 * | 4/2002 | Karami | 604/391 |
| 2002/0111596 A1 * | 8/2002 | Fletcher et al. | 604/385.03 |
| 2002/0148557 A1 * | 10/2002 | Heller et al. | 156/252 |
| 2003/0055389 A1 * | 3/2003 | Sanders et al. | 604/358 |
| 2003/0120253 A1 * | 6/2003 | Wentzel et al. | 604/392 |
| 2003/0130641 A1 * | 7/2003 | Richlen et al. | 604/385.01 |
| 2003/0176846 A1 | 9/2003 | Karami | |
| 2004/0068246 A1 * | 4/2004 | Rose et al. | 604/385.27 |
| 2004/0144496 A1 | 7/2004 | Mlinar et al. | |
| 2004/0182502 A1 * | 9/2004 | Wagner et al. | 156/204 |
| 2004/0186451 A1 * | 9/2004 | Bishop et al. | 604/385.11 |
| 2006/0069376 A1 * | 3/2006 | Miller et al. | 604/385.201 |
| 2006/0070701 A1 * | 4/2006 | Kobayashi et al. | 156/277 |
| 2006/0118234 A1 * | 6/2006 | Heller et al. | 156/252 |
| 2006/0212019 A1 * | 9/2006 | Otsubo et al. | 604/395 |
| 2007/0038199 A1 * | 2/2007 | Erdman et al. | 604/385.3 |
| 2007/0129700 A1 * | 6/2007 | Yoshida | 604/385.11 |

FOREIGN PATENT DOCUMENTS

| | | |
|---|---|---|
| JP | H5-317356 | 12/1993 |
| JP | H8-511709 | 12/1996 |
| JP | 2000-354609 A | 12/2000 |
| JP | 2002-35029 A | 2/2002 |
| JP | 3090821 | 12/2002 |
| JP | 2003-220092 A | 8/2003 |
| JP | 2004-524929 | 8/2004 |
| JP | 2005-13598 | 1/2005 |
| JP | 2005-522236 | 7/2005 |
| JP | 2005-230330 A | 9/2005 |
| JP | 2005-526530 A | 9/2005 |
| JP | 2005-270359 | 10/2005 |
| JP | 2005-279006 | 10/2005 |
| JP | 2005-304605 A | 11/2005 |
| JP | 2005-312690 | 11/2005 |
| JP | 2006-34402 | 2/2006 |
| JP | H2006-521169 | 9/2006 |
| RU | 2 218 139 C | 12/2003 |
| WO | WO 03/057102 A | 7/2003 |
| WO | WO 2004/084786 A | 10/2004 |

* cited by examiner

UNDERPANTS TYPE DISPOSABLE DIAPER

CROSS-REFERENCE TO RELATED APPLICATIONS

None

STATEMENT REGARDING FEDERALLY SPONSORED RESEARCH

None

BACKGROUND OF THE INVENTION

1. Technical Field

The present invention relates to disposable diapers that can be used both as a tape-fastening type and an underpants type.

2. Related Art

An underpants type disposable diaper has joined portions on both sides that are formed by joining a front body part and a back body part on both side portions thereof, a waist opening and a pair of right and left leg openings, and the diaper is worn by letting both legs of a wearer pass through the waist opening and inserting the same into the leg openings.

A general underpants type diaper cannot be basically adjusted in size or shape. Therefore, resilient and elastic members are used to impart a resilient and elastic force to the diaper in a width direction so that the diaper can be changed in shape according to the body size of a wearer to thereby offer an increased fit.

Meanwhile, there are provided diapers called fastening type or tape-fastening type that are fitted to a wearer in a state where back and ventral parts are not joined, and fixed at leading ends of fastening tapes on both side portions of the back part to an external surface of the ventral part in use.

In addition, as described in Patent Document 1, there have been suggested two-way disposable diapers that can be used both as an underpants type and a fastening type. Such a disposable diaper has a rear back part, a front belt part extending from the rear back part to both sides in a width direction, and an absorbent main unit that can be folded from the rear back part through a crotch toward a front ventral side of a wearer. The diaper can be worn in a state where the front belt part winding around the waist and the folded absorbent main unit are fastened on the front ventral side of the wearer.

Patent Document 1: JP 2005-270359 A

However, such conventional diapers are difficult to adjust in size in a laterally balanced manner when a wearer lies on his/her side.

Specifically, if a wearer lies on his/her side, when an attempt is made to pull up a conventional diaper from upper and lower fastening tapes, the diaper can hardly be extended because a portion around the lower fastening tape is pressed and immovable against a waist of the wearer. In contrast, the diaper can be freely extended at a portion around the upper fastening tape that is not fixed. When being worn without size adjustment, the conventional diaper is extended approximately evenly around the waist. Therefore, if the evenly extended diaper is further extended only at one portion, the diaper may become significantly unbalanced on the right and left sides.

In addition, if a conventional two-way disposable diaper that can serve both as an underpants type and a fastening type, is used as a tape-fastening type, there is a problem that the diaper does not fit sufficiently to a wearer of a nonstandard body size because the tapes cannot be freely attached.

SUMMARY OF THE INVENTION

Therefore, a main object of the present invention is to provide an underpants type disposable diaper that, even if a wearer lies on his/her side, can be adjusted in width in a balanced manner and used both as a tape-fastening type and an underpants type with an excellent fit.

The present invention to solve the foregoing problems is as follows:

First Embodiment

An underpants type disposable diaper, comprising: a front body part and a back body part which are jointed to each other at both side portions thereof to thereby form joined portions on both sides, a waist opening, and a pair of right and left leg openings; and a plurality of elongated resilient and elastic members which are fixed in an area covering from the waist opening to the leg openings at the front and back parts in an extended state in a width direction, wherein perforated lines are formed on the both side portions of the front body part or back body part so as to extend from an edge of the waist opening to edges of the leg openings, the resilient and elastic members are arranged on both sides of the perforated lines such that ends thereof facing to the perforated lines are placed at the same positions as the perforated lines or near the perforated lines, and at least one pair of fastening tapes having engagement sections on inner surfaces thereof straddles the perforated lines.

The underpants type disposable diaper in the present invention can be used as an underpants type when the diaper is not torn along the perforated lines, and can be used as a tape-fastening type when the diaper is torn along the perforated lines and connected on the ventral and back sides with the fastening tapes. Particularly, in providing the underpants type diaper with a plurality of long narrow (elongated) resilient and elastic members in a width direction in an area covering from the waist opening to the leg openings at the front and back body parts for an improved fit to a waist, if the resilient and elastic members are continuous across the perforated lines, the both sides of perforated lines remain connected due to the resilient and elastic members even though the diaper is tore along the perforated lines. In the present invention, however, the resilient and elastic members are arranged on the both sides of perforated lines in such a manner that the leading ends thereof facing to the perforated lines are located at the same positions as the perforated lines or near the perforated lines, and do not extend beyond the perforated lines. Therefore, the resilient and elastic members do not prevent the diaper from being torn along the perforated lines.

By providing resilient and elastic members in a direction that crosses the perforated lines, the diaper offers an improved fit to the body of a wearer. However, when the conventional diaper is being used as an underpants type, a contraction force of the resilient and elastic members acts in a direction that opens up the perforated lines when wearing the diaper, and thus the diaper may be unintentionally torn along the opened perforated lines. To solve this problem, the fastening tapes are fixed across the perforated lines so as to connect the both sides of the perforated lines, thereby preventing the diaper from being separated.

In addition, if the diaper is shortened in width using fastening tapes in excess of a contraction capacity offered by the resilient and elastic members, excessive wrinkles may be formed in the diaper to thereby produce a large clearance between the diaper and the body of a wearer. Needless to say, such a clearance leads to leakage of a liquid. To solve this problem, the present invention advantageously provides the perforated lines so that the diaper can be significantly shortened in width, without impairing a fit to the body of a wearer, by tearing the diaper along the perforated lines and overlapping the both torn ends as appropriate.

Further, even at night or in winter, the diaper as an underpants type diaper generally needs to be fit to a wearer who has completely taken off his/her bottoms (trousers). However, the diaper in the present invention can be torn along the perforated lines on the both sides in the width direction and separated. Accordingly, the diaper in the present invention can be used by attaching the separated parts with the tapes, without having to completely take off the bottoms (trousers) from the wearer.

Another Embodiment

In the underpants type disposable diaper according the present invention, the resilient and elastic member is fixed so as to cross the perforated line in an extended state in a direction of crossing, and then cut at the same position as the perforated line or near the perforated line.

Rather than using the previously cut resilient and elastic member, it is preferable for ease of manufacture to attach and then cut the resilient and elastic member.

Another Embodiment

In the underpants type disposable diaper according the present invention, the elongated resilient and elastic member is fixed only at a portion that overlaps the engagement section of the fastening tape and a portion near the overlapping portion, in an extended state in a direction that crosses the perforated line, and the engagement sections are detachably engaged so as to straddle both sides of the perforated lines.

In the present invention, the long narrow (elongated) resilient and elastic members are fixed only at portions overlapping the engagement sections of the fastening tapes and portions near the overlapping portions in the extended state in the direction that crosses the perforated lines, and the engagement sections of the fastening tapes are engaged so as to straddle the both sides of the perforated lines, whereby it is possible to prevent the diaper from being separated along the perforated lines as stated above in a more reliable and effective manner. Further, since the fastening tapes need to be engaged only at required portions, it is possible to reduce usage amount of the expensive fastening tapes as much as possible.

Additionally, in such an arrangement as in the present invention, the diaper can be used such that the fastening tape on one side is disengaged by tearing the diaper along the perforated line and then re-engaged the same at a desired position, whereas the fastening tape on the other side remains engaged.

Another Embodiment

In the underpants type disposable diaper according to the present invention, one end of the fastening tape is fixed at the joined portion, and the perforated line is formed so as to pass between an engaged position of the engagement section of the fastening tape and the one end of the fastening tape.

By fixing the base ends of the fastening tapes to the joined portions, it is possible to fix the fastening tapes concurrently with joining of the two body parts. This realizes ease of manufacture and allows the fastening tapes to be more strongly fixed.

Another Embodiment

In the underpants type disposable diaper according to the present invention, the fastening tape is detachably engaged on the external surface of the diaper by the engagement section, and is completely separated from the external surface of the diaper by releasing the engagement.

According to the present invention, the fastening tape can be completely separated from the external surface of the diaper, which allows the fastening tape to be freely attached at any position when the diaper is used as a tape-fastening type. Therefore, the diaper can be used with the fastening tape at freely changeable positions and angles, and thus can be fit to wearers of various body sizes. In addition, the fastening tape can be partly detached for size adjustment. Alternatively, the fastening tape can be removed from the diaper without tearing the diaper along the perforated line. For example, the fastening tape can be used as a retaining material to roll up an unused diaper in a compact size, or can be used as a disposal tape to roll up a used diaper to be discarded.

Another Embodiment

In the underpants type disposable diaper according to the present invention, a plurality of engagement sections are arranged with a predetermined spacing there between on the inner surface of the fastening tape.

According to the arrangement described in this embodiment, it is possible to use the expensive fastening tapes at minimum in size.

Another Embodiment

In the underpants type disposable diaper according to the present invention, the fastening tape is elastically resilient at at least a portion of each area between the engagement sections.

In the present invention, at least a portion of the area between the engagement sections in the fastening tape is configured as to be elastically resilient, which realizes an improved fit and an increased degree of freedom in size adjustment. In using the diaper as a tape-fastening type, the fastening tapes are engaged by the engagement sections with the ventral and back parts separated along the perforated lines, to thereby connect the ventral and back parts. This makes a maximum length of a waist larger than that of the diaper as an underpants type.

Another Embodiment

In the underpants type disposable diaper according to the present invention, when the front and back body parts are under elastic deformation in the width direction) a tensile stress on one body part with the fastening tapes is larger than a tensile stress on the other body part without the fastening tapes.

In the present invention, when the body part with the fastening tapes is larger in tensile stress under elastic deformation in the width direction than the body part without the fastening tapes, the body part with the fastening tapes is contracted and the body part without the fastening tapes is extended. As a result, when the diaper is used without adjustment, the diaper is shortened in width in advance (shortened around the waist) only by a difference in tensile stress, and the both side portions of the body part with the fastening tapes are positioned together with the fastening tapes so as to be closer to a middle area of the diaper in the width direction.

Accordingly, even if a wearer lies on his/her side, the diaper is, extended in advance near the lower fastening tape, and thus the diaper is less prone to become unbalanced even when the upper fastening tape is pulled on for width adjustment. In addition, since the fastening tapes are positioned closer to the middle area of the diaper in the width direction, the wearer can easily pick up the fastening tapes to adjust the width of the diaper by his/her own.

Incidentally, the tensile stress under elastic deformation in the present invention refers to a tensile stress that is generated when the diaper is contracted by 15% with respect to the width of the body part stretched at maximum in the width direction.

Another Embodiment

In the underpants type disposable diaper according to the present invention, the plurality of fastening tapes are provided on each of the both side portions of the front body part or back body part.

By providing the plurality of fastening tapes on each of the both side portions, it is possible to further improve a fit of the diaper used as a tape-fastening type and allow the diaper to be fit to a greater variety of body size.

Another Embodiment

In the underpants type disposable diaper according to the present invention, the fastening tape has at least one perforated line and can be separated into a plurality of fastening tapes by tearing along the perforated line.

Such an arrangement as described above provides ease of manufacture even in the case of increasing the number of the fastening tapes.

As stated above, the present invention provides advantageously a diaper that can be used as a tape-fastening type and an underpants type, offers an excellent fit, allows width adjustment in a balanced manner even a wearer lies on his/her side, and others.

DETAILED DESCRIPTION OF THE INVENTION

Embodiments of the present invention will be described in detail with reference to the drawings.

First Embodiment

Figure 1:
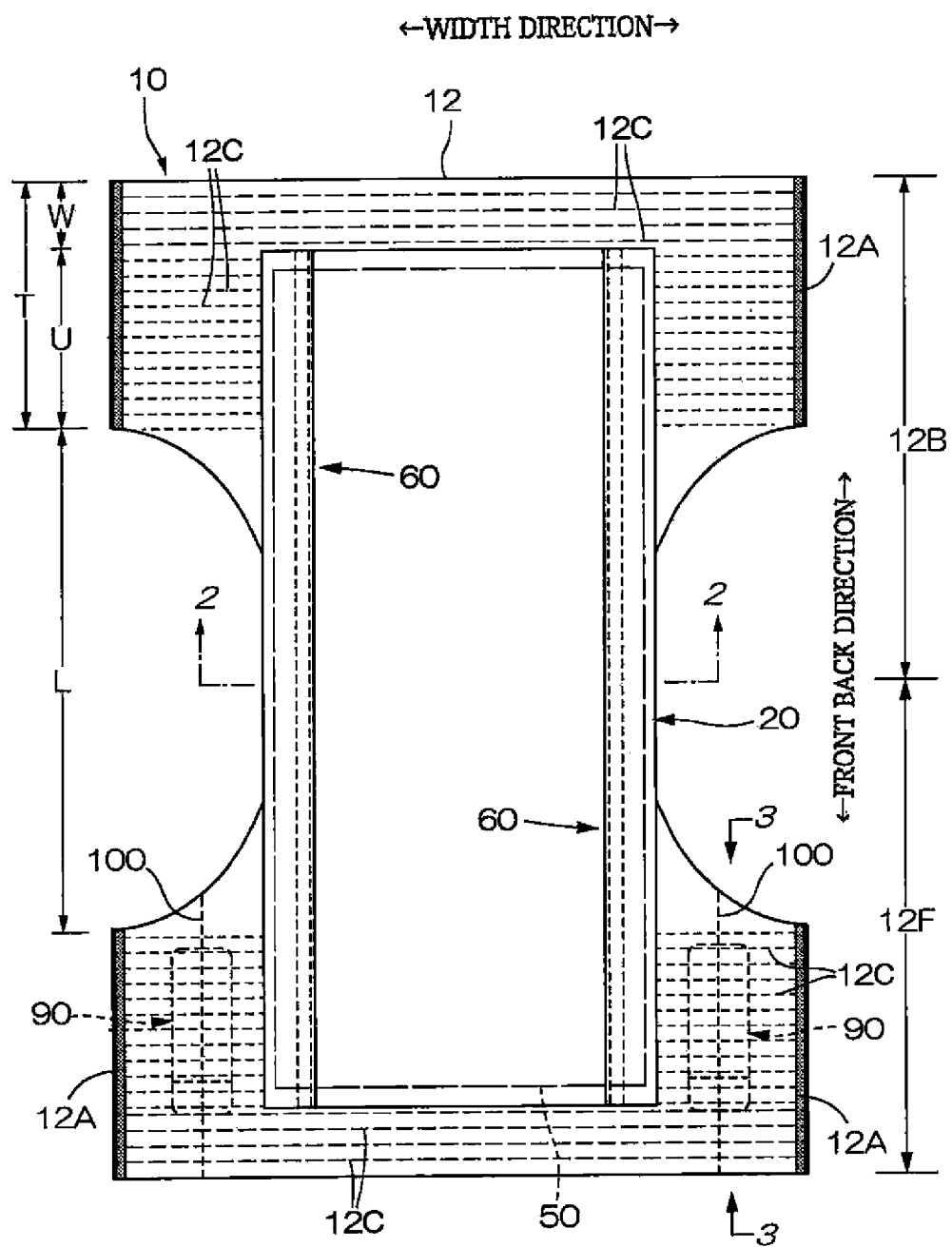
FIG. 1 is a developed plan view of an inner surface of a first embodiment.

FIG. 1 shows an example of an underpants type disposable diaper. The underpants type disposable diaper 10 includes an outer sheet 12 on an external (back) side and an absorbent main unit 20 on an inner (face) side, the absorbent main unit 20 being fixed to the outer sheet 12. The absorbent main unit 20 receives, absorbs and retains excreted objects such as urine and loose stool, and extends to a crotch and portions near a waist opening WO on both front and back sides of the crotch. The outer sheet 12 fits the absorbent main unit 20 to the body of a wearer.

The outer sheet 12 is shaped like an hourglass, for example, that has constrictions on both sides as shown in the diagram, from which legs of a wearer enter. The absorbent main unit 20 may take any shape, and is rectangular in the illustrated embodiment.

Figure 4:
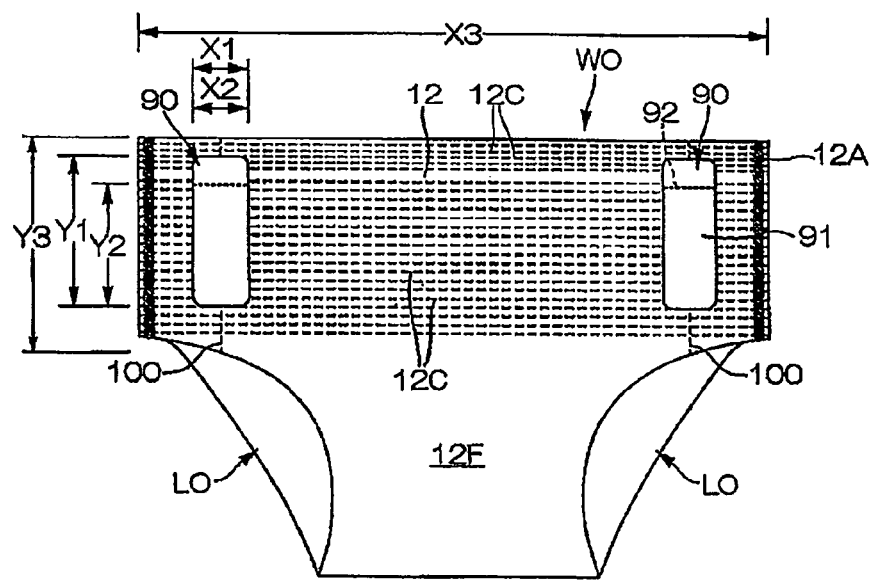
FIG. 4 is a front view of a final product state.

After the absorbent main unit 20 is placed and fixed in a predetermined position, the outer sheet 12 is folded vertically, and then the front body part 12F and the back body part 12B which are jointed to each other by heat sealing and the like at both side portions thereof to thereby form joined portions 12A on both sides, as shown in FIG. 4. This achieves an underpants type disposable diaper with the waist opening WO and a pair of leg openings LO, that is configured as shown in FIG. 1.

In the illustrated embodiment, a width of a middle portion of the absorbent main unit 20 in a longitudinal direction (that is, a vertical direction in FIG. 1, and also a front-back direction of the diaper) is longer than a width of a constricted portion of the outer sheet 12. This relation between the two widths may be reversed, or the two widths may be the same.

In FIG. 1, the term "front-back direction" refers to a direction that connects a ventral side to a back side, and the term "width direction" refers to a direction that is orthogonal to the front-back direction. The term "waist opening edge" refers to an edge of the waist opening WO, and the term "leg opening edge" an edge of the leg opening LO. The term "leg opening starting end" refers to a position where the leg opening edge of the leg opening LO crosses a joined portion 30, which means a starting point of the leg opening edge. The term "around-waist portion" T refers to an entire longitudinal area covering from the waist opening edge to the leg opening starting end. The around-waist portion T is conceptually divided into a "waist portion" W and an "under waist portion" U. The lengths of these portions in the front-back direction depend on the size of the diaper: the waist portion W is 15 to 40 mm; and the under waist portion U is 45 to 220 mm. The term "crotch" L refers to an area forming the leg opening, that is, an entire longitudinal area covering from the leg opening starting end of the front body part to the leg opening starting end of the back body part. The term "middle portion" refers to a middle area including a center line of the diaper, except for side portions. The term "side edge portions" refer to both side edge portions of the around-waist portion T.

The outer sheet 12 is desirably formed by laminating two nonwoven fabrics as shown in the diagram. In a desired mode, long narrow resilient and elastic members 12C are fixed in an extended state between the nonwoven fabrics so that the outer sheet 12 is fitted to the body of a wearer by a stretching force of the resilient and elastic members 12C. The resilient and elastic members 12C may be belt-shaped rubber threads or elastic foam, but are desirably a large number of rubber threads. In the illustrated mode, a plurality of rubber threads 12C, 12C . . . are provided in parallel at the waist portion W so as to be continuous in the width direction, are provided in parallel only at both side portions of the under waist portion U so as to be continuous in the width direction, and are not provided at the middle portion overlapping the absorbent main unit 20. By providing the rubber threads 12C, 12C . . . at both the waist portion W and the under waist portion U, the diaper fits favorably to the body of a wearer.

(Absorbent Main Unit)

Figure 2:
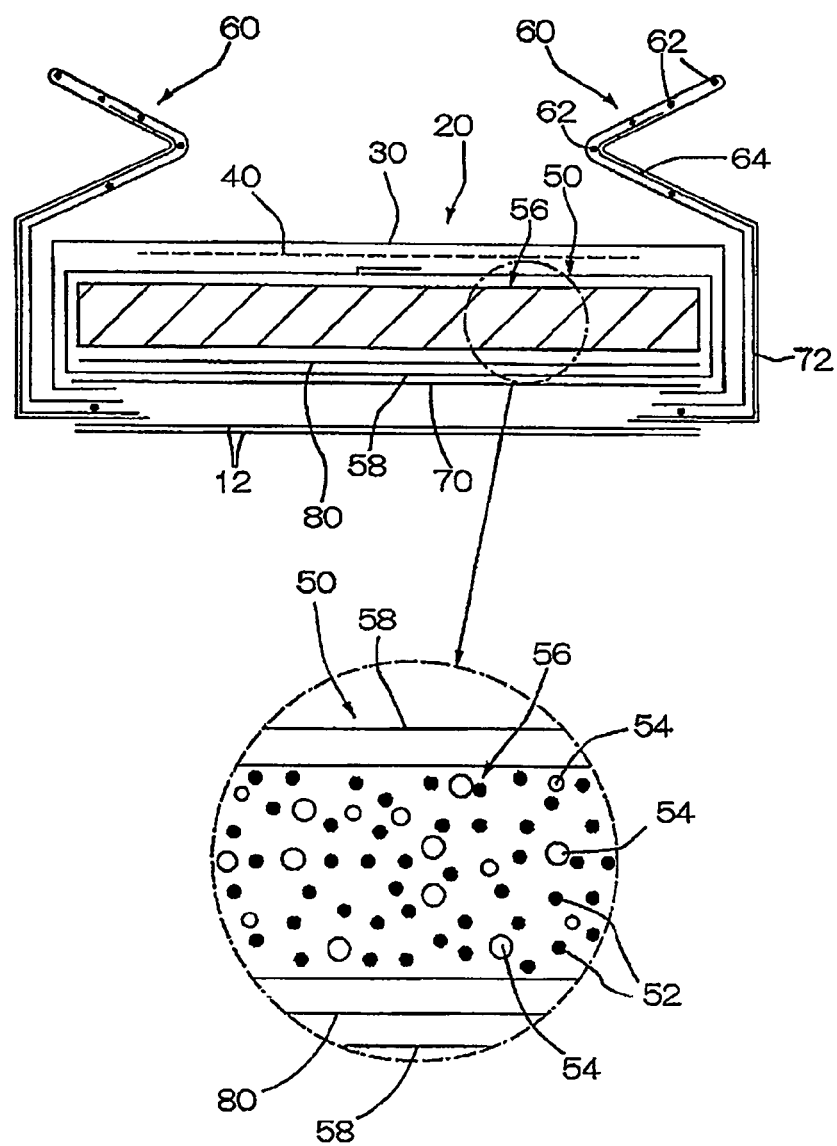
FIG. 2 is a cross-sectional view of FIG. 1 taken along 2-2.

The absorbent main unit 20 may include a top sheet 30 formed of a liquid pervious nonwoven fabric for example, and an absorbent element 50, in this order from a usage side as shown in FIG. 2. In general, a liquid impervious sheet 70 formed of a plastic sheet or the like is provided on an under side of the absorbent element 50. The liquid impervious sheet 70 is joined on an under side to a body-side of the outer sheet 12. In addition, an interlayer sheet (second sheet) 40 may be provided between the top sheet 30 and the absorbent element 50 so that a liquid having permeated through the top sheet 30 can rapidly move to the absorbent element 50. Further, erected barrier cuffs 60, 60 may be provided on both sides of the absorbent portion 20 to thereby prevent an excreted object from leaking to the both sides of the absorbent portion 20. Although not shown, the foregoing constitutional members of the absorbent main unit 20 can be fixed to one another by solid, bead or spiral application of a hot-melt adhesive or the like.

The absorbent main unit 20 can be detachably attached to the outer sheet 20 by a mechanical fastener or an adhesive material.

(Top Sheet)

The top sheet 30 has a liquid pervious property. Therefore, a material for the top sheet 30 only needs to have liquid perviousness, and may be a porous or nonporous nonwoven fabric or a porous plastic sheet, for example. In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton, mixed or composite fibers of two or more of the foregoing fibers. Further, the nonwoven fabric may be produced by any processing method. For example, such a processing method may be any known method such as a spun lace method, spun bonding method, thermal bonding method, melt-blown method, needle punching method, air-through method, or point bonding method. For example, if flexibility and drape property are needed, the spun lace method or the spun bonding method is preferred. If high bulk and softness are required, the air-through method, the point bonding method, or the thermal bonding method is preferred.

In addition, the top sheet 30 may be a single sheet or a laminated sheet obtained by sticking two or more sheets to each other. Similarly, the top sheet 30 may be a single sheet or two or more sheets in a planar direction.

(Interlayer Sheet)

To rapidly move a liquid having permeated through the top sheet 30 to the absorbent body, an interlayer sheet (also called "second sheet") 40 may be provided, which is higher in liquid permeability rate than the top sheet 30. The interlayer sheet 40 allows a liquid to move quickly to the absorbent body to thereby enhance an absorption performance of the absorbent body, and prevents a "backflow" phenomenon in which a liquid flows back from the absorbent body to thereby keep the top sheet 30 in a dry condition. The interlayer sheet 40 may be omitted.

The interlayer sheet 40 may use the same material as that for the top sheet 30, or may use a spun lace, a pulp nonwoven fabric, a mixed sheet of pulp and rayon, point-bonded or crepe paper, for example. In particular, an air-through nonwoven fabric or a spun-bonded nonwoven fabric is preferred.

Although, in the illustrated embodiment, the interlayer sheet 40 is made shorter in width than the absorbent body 56 and is centered with respect to the absorbent body 56, the interlayer sheet 40 may also be provided across an entire width of the absorbent body 56. A length of the interlayer sheet 40 in the longitudinal direction may be the same as that of the absorbent body 56, or may be in a shorter range centered in an area for receiving a liquid. A typical material for the interlayer sheet 40 is a highly liquid pervious nonwoven fabric.

(Liquid Impervious Sheet)

The liquid impervious sheet 70 simply refer to a sheet provided on an under side of the absorbent body 56, and the absorbent element 56 is interposed between the liquid impervious sheet 70 and the top sheet 30 in this embodiment. There is thus no particular limitation on a material for the liquid impervious sheet 70. Specifically, the material may be any of olefin resins such as polyethylene and polypropylene, laminated nonwoven fabrics in which a nonwoven fabric is laminated on a polyethylene sheet or the like, and nonwoven fabrics to which a water-proof film is interposed for virtual liquid imperviousness (in this case, the water-proof film and the nonwoven fabric constitute a liquid impervious sheet), for example. Certainly, in addition to the foregoing examples, there are liquid impervious, moisture pervious sheets that have been favorably used in recent years from the viewpoint of prevention of stuffiness. Such a sheet made of a liquid impervious and moisture pervious material may be a microporous sheet obtained by melting and kneading an inorganic filling agent into an olefin resin such as polyethylene or polypropylene, to thereby form a sheet and then extending the sheet in a uniaxial or biaxial direction, for example.

The liquid impervious sheet 70 can be extended to the usage surface (not shown) so as to wrap around the sides to thereby prevent lateral leakage of a liquid. In this embodiment, lateral leakage is prevented by interposing a second liquid impervious sheet 72 in the double barrier sheet 64 forming barrier cuffs 60. According to this embodiment, since the second liquid impervious sheet 72 extends to erected portions of the barrier cuffs 60, it is possible to advantageously prevent that lateral diffusion of a liquid along the top sheet 30 and lateral leakage of loose stool between the barrier cuffs 60 and 60.

The liquid impervious sheet 70 may include an indicating section with a product name, description of a function, a cartoon character, a pattern and the like. The indicating section may have a function of indicating voiding of urine.

(Barrier Cuffs)

The barrier cuffs 60, 60 on the both sides of the absorbent article are designed to block and prevent urine or loose stool from moving and leaking laterally over the top sheet 30. The barrier cuffs 60, 60 are additional elements.

The illustrated barrier cuffs 60 are formed by laminating two water repellent nonwoven fabric sheets so as to cover from the under side of the absorbent body 56 to a downward folded portion of the top sheet 30, and project toward the upper side of the absorbent body 56. To block urine moving laterally over the top sheet 30, the second liquid impervious sheet 72 is interposed between the two nonwoven fabric sheets forming the barrier cuffs 60. Although not shown, the liquid impervious sheet 70 may be inserted at side portions into the two laminated nonwoven fabric sheet, and extended to midpoints in the barrier cuffs 60 projecting toward the upper side.

The barrier cuffs 60 can be designed in shape as appropriate. In the illustrated example, the resilient and elastic members, e.g., rubber threads 62 are fixed in an extended state at the leading ends and middle portions of projections of the barrier cuffs 60 so that the barrier cuffs 60 are erected by a stretching force of the rubber threads 62 when the diaper is being used. In this mode, the rubber threads 62 at the middle portions are located closer to a center of the top sheet 30 as compared with the rubber threads 62, 62 at the leading ends, and are fixed at front and back ends of the top sheet 30, and therefore the barrier cuffs 60 are erected at base portions in such a manner as to be slant to the center, and are erected at the middle portions to the leading ends in such a manner as to be slant outward as shown in FIG. 2.

(Absorbent Element)

The absorbent element 50 has an absorbent body 56, and an envelope sheet 58 that envelops at least an under surface and side surfaces of the absorbent body 56. The envelope sheet 58 may be omitted. Further, in the illustrated embodiment, a holding sheet 80 is disposed between the absorbent body 56 and the envelope sheet 58 on the under side (lower side). The holding sheet 80 may be omitted.

(Absorbent Body)

The absorbent body 56 may be an accumulation of short fibers of fluff pulp or the like, an assembly of filaments 52, 52 . . . , or others.

The assembly of filaments 52, 52 . . . can be obtained by opening a tow (fiber bundle). Constitutional fibers for the tow may be any of polysaccharides or derivatives thereof (such as cellulose, cellulose ester, chitin, and chitosan), synthetic polymers (such as polyethylene, polypropylene, polyamide, polyester, polylactamide, and polyvinyl acetate) and the like, for example. In particular, cellulose ester or cellulose is preferable.

Usable celluloses include celluloses derived from plants such as cotton, linters and wood pulp, bacterial celluloses, and regenerated celluloses such as rayon. Regenerated celluloses may be in the form of spun fibers.

Preferably used cellulose esters include: organic acid esters such as cellulose acetate, cellulose butyrate, and cellulose propionate; mixed acid esters such as cellulose acetate propionate, cellulose acetate butyrate, cellulose acetate phthalate, and cellulose nitrate acetate; cellulose ester derivatives such as polycaprolactone grafted cellulose ester; and the like. These cellulose esters may be used singly or in combination. A viscosity average degree of polymerization of a cellulose ester is about 50 to 900 for example, preferably about 200 to 800. An average degree of substitution of a cellulose ester is about 1.5 to 3.0 (e.g. 2 to 3), for example.

An average degree of polymerization of a cellulose ester may be about 10 to 1,000 for example, preferably about 50 to 900, and more preferably about 200 to 800. An average degree of substitution of a cellulose ester may be about 1 to 3 for example, preferably about 1 to 2.15, and more preferably about 1.1 to 2.0. An average degree of substitution of a cellulose ester may be selected from a viewpoint of enhancing biodegradability.

Cellulose ester may be an organic acid ester (ester of organic acid with a carbon number of about 2 to 4, for example), and is preferably in particular a cellulose acetate. An acetylation degree of a cellulose acetate is about 43 to 62% in many cases, and preferably in particular about 30 to 50% with higher biodegradability. A particularly preferred cellulose ester is cellulose diacetate.

The tow constitutional fibers may contain various additives, for example, a heat stabilization agent, coloring agent, oil solution, retention aid, whiteness improving agent, and the like.

A fineness of the tow constitutional fibers is 1 to 16 deniers for example, preferably 1 to 10 deniers, and more preferably 1 to 6 deniers. The tow constitutional fibers may be non-crimped fibers but preferably crimped fibers. A degree of crimping of the crimped fibers may be about 5 to 75 crimps per inch, preferably about 10 to 50 crimps per inch, and more preferably about 15 to 50 crimps per inch. In many cases, uniformly crimped fibers are used. By using such crimped fibers, it is possible to produce a high-integration tow due to fiber entanglement, and manufacture a high-bulk, lightweight absorbent body. There is no particular limitation on a cross-section shape of the tow constitutional fibers, and the tow constitutional fibers may be circular, elliptic, odd (e.g. Y, X, I, or R letter) or hollow in cross section, for example. The tow constitutional fibers can be used as a tow (fiber bundle) of about 1,000 to 1,000,000 single fibers for example, preferably about 2,000 to 1,000,000 single fibers. Such a fiber bundle is preferably formed by binding about 1,000 to 1,000,000 continuous fibers.

Bales of tow of cellulose diacetate preferably used in the present invention are made commercially available by Celanese Corp., Daicel Chemical Industries, Ltd., and others. A bale of tow of cellulose diacetate is about 0.5 g/cm$^3$ in density and 400 to 600 kg in gross weight. The tow is peeled off from the bale and opened in a wide belt-like form of desired size and bulk. An opening width of the tow can be arbitrarily decided, for example 50 to 2,000 mm, preferably about 50 to 300 mm, so as to be adapted to the width of the absorbent body in the diaper. In addition, the density of the absorbent body can be adjusted by controlling a degree of tow opening.

Preferably, high-absorbent polymer particles 54, 54 . . . are contained in the absorbent body 56, as shown in FIG. 2. In addition, at least in an area receiving a liquid, high-absorbent polymer particles (SAP particles) are desirably scattered in a virtually overall thickness direction with respect to the assembly of filaments 52, 52 . . . . FIG. 2 is a conceptual enlarged view of the particles scattered in the virtually overall thickness direction.

If there are no or few if any, SAP particles in upper, lower and middle portions of the absorbent body 56, it is not recognized that "the SAP particles are scattered in the overall thickness direction". Therefore, the "scattered in the overall thickness direction" state refers to a mode in which the particles are scattered "evenly" in the overall thickness direction with respect to the assembly of filaments, or a mode in which the particles are "unevenly distributed" in the upper, lower and/or middle portions but still are scattered in the upper, lower and/or middle portions. In addition, the foregoing state does not exclude a mode in which some of the SAP particles does not enter into the assembly of filaments 52, 52 ... and remain on a surface of the same, or a mode in which some of the SAP particles pass through the assembly of filaments 52, 52 ... and exist on the envelope sheet 58 or the holding sheet 80.

(High-absorbent Polymer Particles)

The high-absorbent polymer particles 54 may be not only "particles" but also "powders". A particle diameter of the high-absorbent polymer particles 54 may be the same as that of particles used in this kind of absorbent articles, and is 1,000 µm or less, desirably in particular 150 to 400 µm. There are no particular limits on a material for the high-absorbent polymer particles 54, and a preferred material is 40 g/g or more in capacity of water absorption. The high-absorbent polymer particles 54 may be based on starch, cellulose or synthetic polymer, and may use starch-acrylic acid (salt) graft copolymer, saponified product of starch-acrylonitrile copolymer, cross-linked sodium carboxymethyl cellulose, acrylic acid (salt) polymer, or the like. A shape of the high-absorbent polymer particle 54 is preferably a commonly used particulate shape, and may also be any other shape.

The high-absorbent polymer particles 54 preferably deliver a water absorption speed of 40 seconds or less. If the water absorption speed exceeds 40 seconds, a backflow phenomenon becomes prone to occur, where a liquid having been supplied to the absorbent body 56 flows back out of the absorbent body 56.

In addition, the high-absorbent polymer particles 54 are preferably 1,000 Pa or more in gel strength. This prevents effectively a sticky feel after absorption of a liquid even if the absorbent body 56 is high in bulk.

A basis weight of the high-absorbent polymer particles 54 may be decided as appropriate in accordance with an absorption capacity required for the absorbent body 56, and may be 50 to 350 g/m$^2$, although it is not always defined so. By setting the basis weight of the polymers at 50 g/m$^2$ or less, it is possible to prevent that weight reduction becomes less effective due to the weight of the polymers when synthetic continuous fibers are used. If the basis weight exceeds 350 g/m$^2$, the high-absorbent polymer particles 54 become saturated in effectiveness and an excessive amount thereof has an unpleasant grainy feel.

If necessary, the high-absorbent polymer particles 54 can be adjusted in dispersing density or dispersing amount in the planar direction of the absorbent body 56. For example, an amount of dispersion may be made larger at a liquid excreted portion than other portions. With regard to a difference between the sexes, the dispersion density (amount) may be increased at the front side portion for men and increased at the middle portion for women. The absorbent body 56 may have a local portion (in spot, for example) with no polymer in the planar direction thereof As needed, a plurality of high-absorbent polymer particles 54 with different particle size distributions can be provided in sequence in the thickness direction, such that the particles with smaller particle size distributions are located on the lower portion of the absorbent body 56, and the particles with larger particle size distributions on the upper portion of the same.

Proportions of the high-absorbent polymer particles 54 and the continuous fibers affect an absorbing property. A weight ratio of the high-absorbent polymer particles to the continuous fibers in a planar area of 5×5 cm directly receiving a liquid in the absorbent body 56, is 1 to 14, desirably 2 to 9 in particular.

(Envelope Sheet)

The envelope sheet 58 may use any of materials such as tissue paper, particularly crepe paper, nonwoven fabrics, polyethylene-laminated nonwoven fabrics, foraminous sheets, and the like. The sheet desirably does not let high-absorbent polymer particles pass through. In using a nonwoven fabric instead of crepe paper for the envelope sheet 58, a hydrophilic SMMS (spun bonded/melt-blown/melt-blown/spun-bonded) nonwoven fabric is preferred in particular. A material for such a fabric may be polypropylene, polyethylene/polypropylene, or the like. A basis weight of the fabric is 5 to 40 g/m$^2$, desirably 10 to 30 g/m$^2$ in particular.

The envelope sheet 58 may be configured as to envelop an overall layer containing the assembly of continuous fibers 52, 52 ... and the high-absorbent polymer particles 54, 54 ... as shown in FIG. 2, or may envelop only under and side surfaces of the layer. Further, although not shown, the envelope sheet 58 may be configured as to cover the upper and side surfaces of the absorbent body 56 with crepe paper or a nonwoven fabric, and cover the under surface of the same with a liquid impervious sheet of polyethylene or the like, or as to cover the upper surface of the absorbent body 56 with crape paper or nonwoven paper and cover the side and under surfaces of the same with a liquid impervious sheet of polyethylene or the like (the foregoing materials are constitutional elements of the envelope sheet). If necessary, the envelope sheet 58 may be configured in such a manner that the layer containing the assembly of continuous fibers 52, 52 ... and the high-absorbent polymer particles 54, 54 ... is sandwiched between two upper and lower sheets, or in such a manner that one sheet is disposed only on the lower surface of the layer. However, these configurations are not desired because they make it difficult to prevent movement of the high-absorbent polymer particles.

(Holding Sheet)

In providing the holding sheet 80, the high-absorbent polymer particles 54 may be interposed by dispersing or the like between the holding sheet 80 and the absorbent body 56. The high-absorbent polymer particles 54 may pass through the assembly of the continuous fibers 52 during a process of supply to the assembly of the continuous fibers 52, a process subsequent to the foregoing process, or a process of distribution to consumers. The high-absorbent polymer particles having passed through the assembly of continuous fibers may bring an unpleasant grainy feel with asperities thereof to a user who touches the product by hand. To solve this problem, it is preferable to interpose the holding sheet 80 capable of holding the high-absorbent polymers 54 between the absorbent body 56 and the envelope sheet 58. The holding sheet 80 increases elasticity which would not be sufficiently provided by the envelope sheet 58 alone made of tissue paper (crepe paper) or the like, and reduces or prevents an unpleasant feel given to a user who touches the product by hand.

There is no particular limitation on a material for the holding sheet 80, and such a material only needs to be capable of holding the high-absorbent polymers 54. Specifically, the material may be any of nonwoven fabrics, crimped pulp, low-absorbent cotton fibers (e.g. fat cotton fibers, defatted cotton fibers, rayon fibers processed with a water repellent agent or a hydrophobizing agent), polyethylene fibers, polyester fibers, acrylic fibers, polypropylene fibers, silk, cotton, hemp, nylon, polyurethane, acetate fibers, and the like, for example.

If the holding sheet 80 is formed by a nonwoven fabric, the holding sheet 80 is 0.01 to 10.00 gfcm/cm$^2$, preferably 0.01 to 1.00 gfcm/cm² in compression energy, and is 10 to 100%, preferably 70 to 100% in compression resilience, based on test results from KES Test.

A purpose of providing the holding sheet 80 is, as stated above, to hold the high-absorbent polymers 54 which have dropped (slipped) downward from the absorbent body 56, for example. Therefore, the slipped high-absorbent polymers 54 come into contact with a user via the envelope sheet 58 and the holding sheet 80, and thus there is no fear of giving the user an unpleasant grainy feel. In particular, the nonwoven fabric within the above-mentioned ranges of compression energy and compression resilience can perform sufficiently function thereof.

In addition, since the slipped high-absorbent polymers 54 are held by the holding sheet 80 and thus do not move over the envelope sheet 58, there is no fear of uneven absorption capabilities. Particularly, to prevent movement of the high-absorbent polymer particles 54 over the holding sheet 80, the holding sheet 80 may be coated in advance with a sticky hot-melt adhesive or the like. Alternatively, to prevent movement of the high-absorbent polymer particles 54 over the holding sheet 80, the upper surface of the holding sheet 80 (facing to the usage side) may be made rough. For this purpose, the nonwoven fabric may be manufactured in such a manner that a surface thereof is roughed or fluffed by making non-netted, marbling, needle-punching, or brushing.

The holding sheet 80 may be provided only underneath the absorbent body 56 as shown in FIG. 2, or may pass by the absorbent body 56, roll and extend to the upper surface of the absorbent body 56, although not shown. In addition, a stack of a plurality of holding sheets 80 may be used.

Although, in the above example, the holding sheet 58 is disposed between the absorbent body 56 and the envelope sheet 58 on the lower side, the holding sheet may be placed under the envelope sheet instead (this arrangement is not shown). The important point is that providing the holding sheet under the absorbent body 56 reduces or eliminates an unpleasant grainy feel which would be given to a user who touches the product from the under surface thereof.

(Fastening Tapes and Others)

Characteristically, as shown in FIG. 1, perforated lines 100, 100 are formed so as to extend on the both side portions of the around-waist portion T in the front body part 12F from an edge of the waist opening WO to edges of the leg openings LO. The perforated lines 100 can be arranged with any pitch. In addition, it is preferred to provide, by printing or the like, indications for easy recognition of positions of the perforated lines 100.

Figure 3:
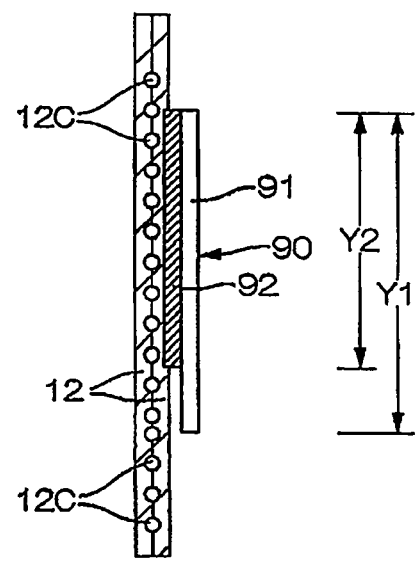
FIG. 3 is a cross-sectional view of FIG. 1 taken along 3-3.

Further characteristically, as shown in FIGS. 1 and 3, fastening tapes 90, 90 are attached to the external surface of the front body part at both portions with the perforated lines 100, respectively. The fastening tape 90 is formed in such a manner that a hook member (hook member of a mechanical fastener) 92 is attached to an inner surface of a belt-shaped base material sheet 91 except for an end portion on one side of the same in a longitudinal direction, and the end portion without the hook member 92 constitutes a pickup portion. The fastening tape 90 is entirely engaged in a separable manner on the external surface of the diaper, in which the hook member 92 becomes entangled in nonwoven fibers in the external surface of the outer sheet 12. The hook member 92 may be a publicly known sheet member that has on a surface thereof a large number of hook projections in the shape of a mushroom, a J letter or the like.

The fastening tape 90 can be decided in shape and size as appropriate, and is preferably belt-shaped as shown in the diagram. A width X1 of the fastening tape 90 (a length in a direction orthogonal to a longitudinal direction) may be about 20 to 80 mm, preferably about 30 to 50 mm. A length Y1 of the fastening tape 90 (in the longitudinal direction) is desirably about 60 to 100% of a length Y3 of the perforated line 100. In addition, a width X2 of the hook member 92 (a length in a direction orthogonal to the longitudinal direction) is desirably about 50 to 100% of the width X1 of the fastening tape 90, and a length of the hook member 92 (in the longitudinal direction) is desirably about 50 to 100% of the length Y1 of the fastening tape 90.

An engagement section of the fastening tape 90 in the final product can be decided as appropriate, and the hook member 92 of the fastening tape 90 preferably straddles the both sides of the perforated line 100. Accordingly, it is possible to prevent that the diaper is unintentionally torn along the perforated line 100 when the diaper is unused or is used as an underpants type. In addition, by making larger a separation strength of the fastening tape around the perforated line than a tear strength of the diaper in the perforated line, it is possible to disengage the fastening tape 90 on one side concurrently with tearing of the diaper along the perforated line 100, and then re-engage the one side of the fastening tape 90 at a desired position, while letting the other side of the fastening tape 90 remain engaged. In particular, the fastening tape 90 is preferably engaged on the external surface of the diaper in such a manner that the longitudinal direction thereof comes along the perforated line 100 since a minimum amount of material can cover the perforated line 100 in a wider area.

As in the illustrated mode, if the resilient and elastic members 12C such as rubber threads are continuous across the perforated line 100, even though the diaper is torn along the perforated lines 100, the diaper remains connected on the both sides of the perforated lines 100 by the resilient and elastic members 12C. Accordingly, to avoid this connection, the resilient and elastic members 12C sandwich the perforated lines 100 therebetween in such a manner that ends thereof facing the perforated lines 100 are positioned on or near the perforated lines 100.

The foregoing arrangement can be formed by: fixing the resilient and elastic members 12C on the outer sheet 12 so as to cross the perforated lines 100 and extend in a direction of crossing; subjecting the outer sheet 12 to needle-stitching, notching, and embossing along the perforated lines 100 at the same positions as those of the perforated lines 100 or near the perforated lines 100; and cutting the resilient and elastic members 12C crossing the perforated lines 100. In particular, it is preferred to cut the resilient and elastic members concurrently with incising of the perforated lines in a perforating process, thereby bringing about ease of manufacture.

In the perforating process, it is preferred to select materials such that fusing points of the hook members 92 and fastening tape base materials 91 are higher by 10° C. or more than a fusing point of a nonwoven fabric of the outer sheet 12, and then form the perforated lines 100 by application of heat or ultrasound concurrently with incising of the perforated lines 100. Alternatively, it is preferred to subject the external surface of the outer sheet 12 and the inner surfaces of the fastening tapes 90 (the hook member 92—side surface) to a fusion inhibitory process by means of a silicon treatment or the like, and then form the perforated lines 100 by application of heat or ultrasound. In forming the perforated lines 100, it is preferred to attach the fastening tapes 90 in predetermined positions with the resilient and elastic members between the nonwoven fabrics and to make an incision from a side opposite to the attachment-side of the fastening tapes 90. As a result, the outer sheet 12 and the fastening tapes 90 are not fused to each other or are fused by a weak force, thereby causing no problem in use. In addition, this brings about an advantage that a manufacturing process becomes not complicated.

In addition, if the front body part 12F and back body part 12B of the outer sheet 12 are jointed on the both sides by heat sealing, the resilient and elastic members 12C on the both sides may be cut by the heat sealing, and brought by contraction thereof toward the middle area of the diaper in the width direction beyond the perforated lines 100.

Further, if the resilient and elastic members 12C are cut in such a manner that the resilient and elastic members 12C are not provided at the portion overlapping the absorbent main unit 20, the resilient and elastic members 12C closer to the middle area of the diaper in the width direction may be brought by the cutting toward the both sides of the diaper in the width direction beyond the perforated line 100. In this case, the resilient and elastic members may be cut concurrently with forming of the perforated lines.

Accordingly, it is possible to prevent that the resilient and elastic members 12C crossing the perforated line 100 inhibit tearing of the diaper along the perforated line 100, thereby realizing ease of manufacture.

The diaper configured as described above can be used as an underpants type without being torn along the perforated line 100 as shown in FIG. 4, or can be used as a tape-fastening type by tearing along the both perforated lines 100, and engaging both ends of the hook members 92 of the fastening tapes 90, 90 in the longitudinal direction or width direction to the ventral and back parts (that is, by joining the ventral and back parts with the fastening tapes 90). If the diaper is used as a tape-fastening type, the both sides of the back part and the both sides of the ventral part may be overlapped or separated. In this case, the fastening tapes 90, 90 are completely separated from the external surface of the diaper, and thus the fastening tapes 90, 90 can be completely freely attached at any positions when the diaper is used as a tape-fastening type. Accordingly, the diaper can be used with freely changeable positions and angles of the fastening tapes 90, 90, and can fit to wearers of various body sizes. In addition, the fastening tape 90 may be partly removed in use for size adjustment. The fastening tape 90 may be completely removed and used for the diaper that is not cut along the perforated line 100. For example, the removed fastening tape 90 may be used as a retaining material to roll up an unused diaper in a compact size, or used as a disposal tape to roll up a used diaper to be discarded.

Second Embodiment

Figure 5:
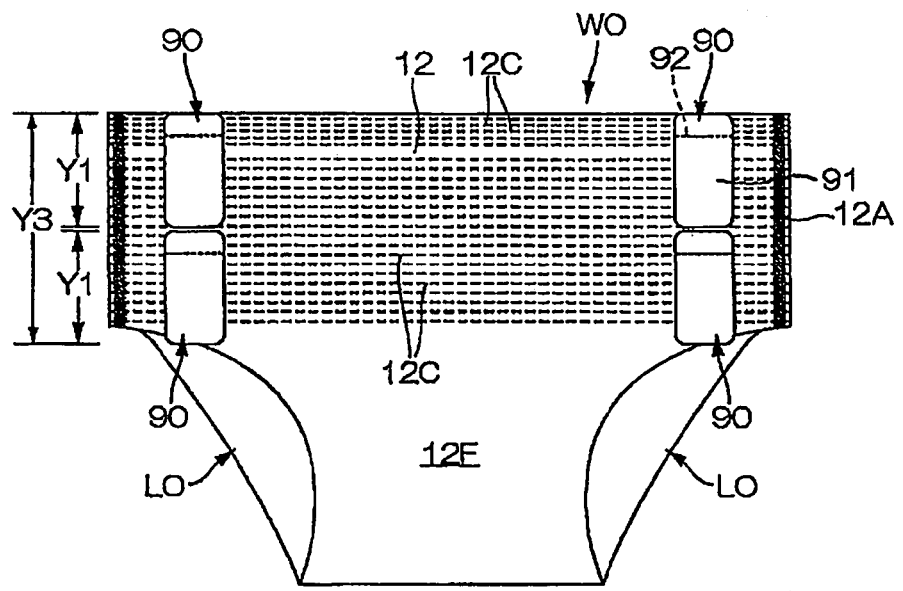
FIG. 5 is a front view of a second embodiment in a final product state.
Figure 6:
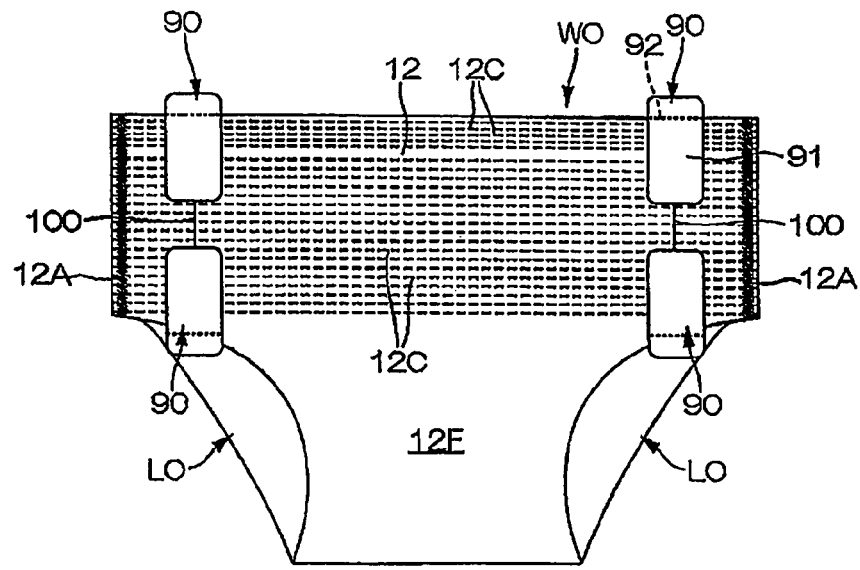
FIG. 6 is a front view of the second embodiment as a tape-fastening type.

As FIG. 5 shows a diaper in a final product state and FIG. 6 shows a diaper as a tape-fastening type, a plurality of fastening tapes 90 may be provided on each of the both side portions of the front body part 12F. In providing a plurality of fastening tapes 90 on each of the both side portions, it is preferred to set a total length Y1+Y1 of all the fastening tapes 90 on one side at about 50 to 100% of a length Y3 of the perforated line 100. Size and shape of the fastening tapes 90 and size of the hook member 90, 90 are the same as those in the first embodiment.

By providing a plurality of fastening tapes 90 for each perforated line as stated above, it is possible to connect the portions separated along the perforated line 100 at two positions (both ends of the perforated line 100 in the example shown in FIG. 6), and set individually orientations of the fastening tapes 90. This further improves a fit of the diaper used as a tape-fastening type and allows the diaper to fit to more body sizes.

Third Embodiment

Figure 7:
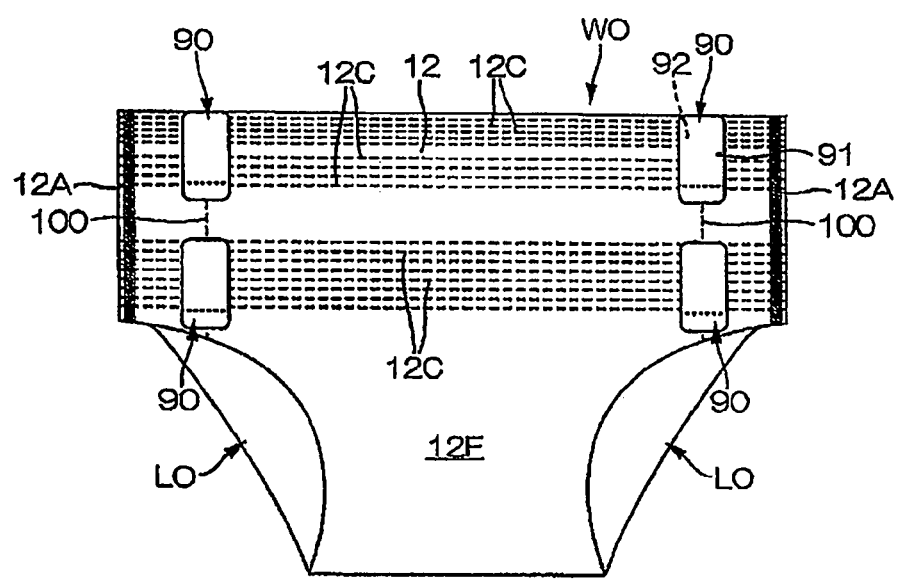
FIG. 7 is a front view of a third embodiment in a final product state.

As shown in FIG. 7, if the resilient and elastic members 12C such as rubber threads cross the perforated lines 100, it is preferred to not only engage the hook members 92 of the fastening tapes 90 detachably across the both sides of the perforated lines 100 but also provide the resilient and elastic members 12C only at portions overlapping the hook members 92 of the fastening tapes and at neighboring portions. This reduces portions that may be unintentionally torn along the perforated lines 100, and thus due to decreased need for prevention of such an unintentional tear, reduces portions on which the fastening tapes 90 are to be engaged. Therefore, it is possible to decrease usage of the expensive fastening tapes 90 to a minimum.

Fourth Embodiment

Figure 8:
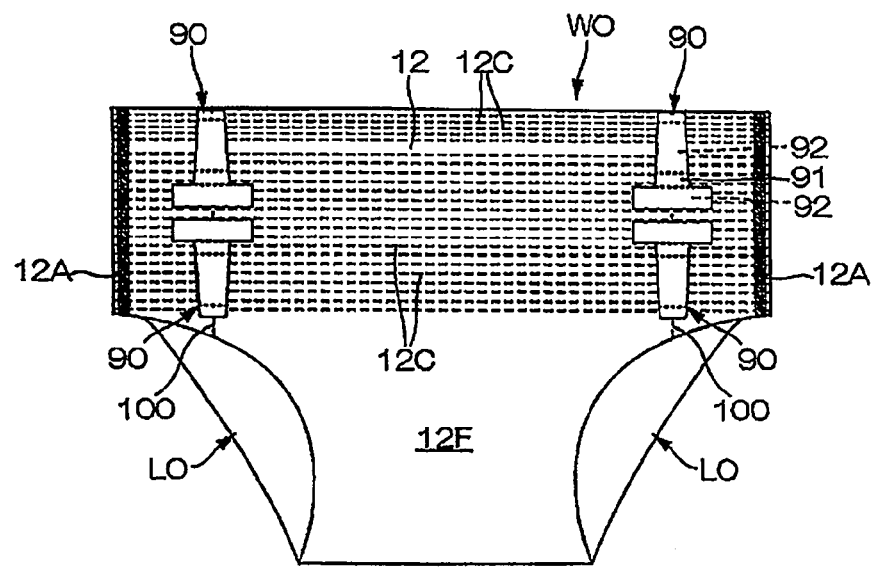
FIG. 8 is a front view of a fourth embodiment in a final product state.
Figure 9:
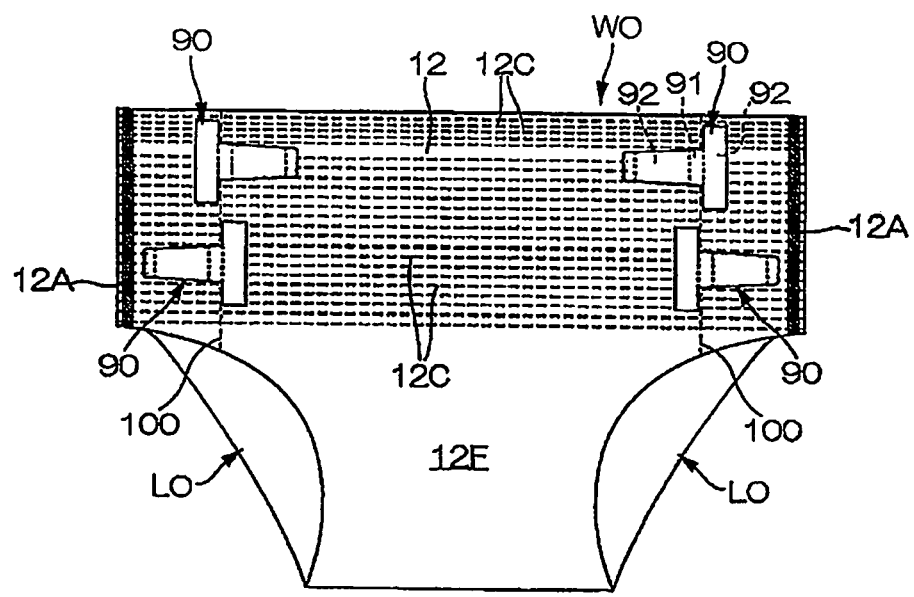
FIG. 9 is a front view of the fourth embodiment as a tape-fastening type.

As FIG. 8 shows a diaper in a final product state and FIG. 9 shows a diaper as a tape-fastening type, a plurality of hook members 92 may be arranged with a predetermined spacing therebetween in the longitudinal direction of the fastening tape 90. In this case, the fastening tape 90 in the final product may be engaged in such a manner that the hook members 92 become intermittent in a direction parallel to a direction of formation of the perforated line 100 (a direction orthogonal to a direction of extension of the resilient and elastic members 12C) and become continuous in a direction orthogonal to the direction of formation of the perforated line 100 (a direction identical to the direction of extension of the resilient and elastic members 12C).

In the fourth embodiment, in a manufacturing process, the resilient and elastic members 12C, the fastening tapes 90, and the hook members 92 can be supplied in one direction to a manufacturing line, and attached to disposable diapers in the direction of the supply without being subjected to a process of 90-degree turning, thereby bringing about ease of manufacture. Additionally, in the present invention, since the entire fastening tape 90 is separated from the external surface of the diaper, the diaper may be turned by 90 degrees after removal of the fastening tape 90 if the diaper is easier to use as a tape-fastening type with a 90-degree turning.

In contrast, the diaper may be configured in such a manner that, in the final product, the hook members 92 are continuous in a direction along the perforated lines 100 and are intermittent in a direction orthogonal to the perforated lines, as shown in FIG. 9. Thus, in the present invention, the fastening tapes 90 can be basically attached in any orientation. The fastening tapes 90 in the final product may be attached in an orientation for use to thereby eliminate the need for changing the orientation in use, or may be attached in an orientation different from the orientation for use so that, in actual use, the fastening tape 90 can be removed and changed to the easier-to-use orientation.

Fifth Embodiment

Figure 10:
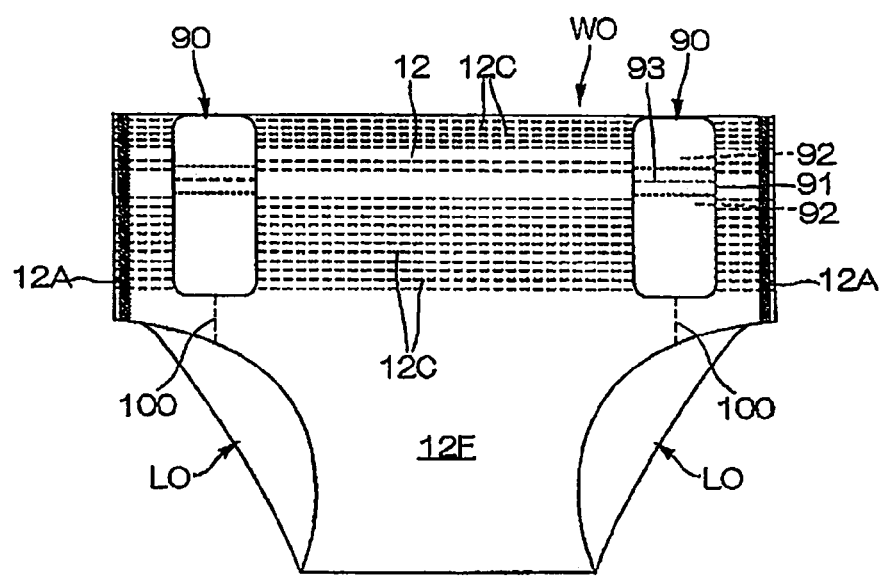
FIG. 10 is a front view of a fifth embodiment in a final product state.
Figure 11:
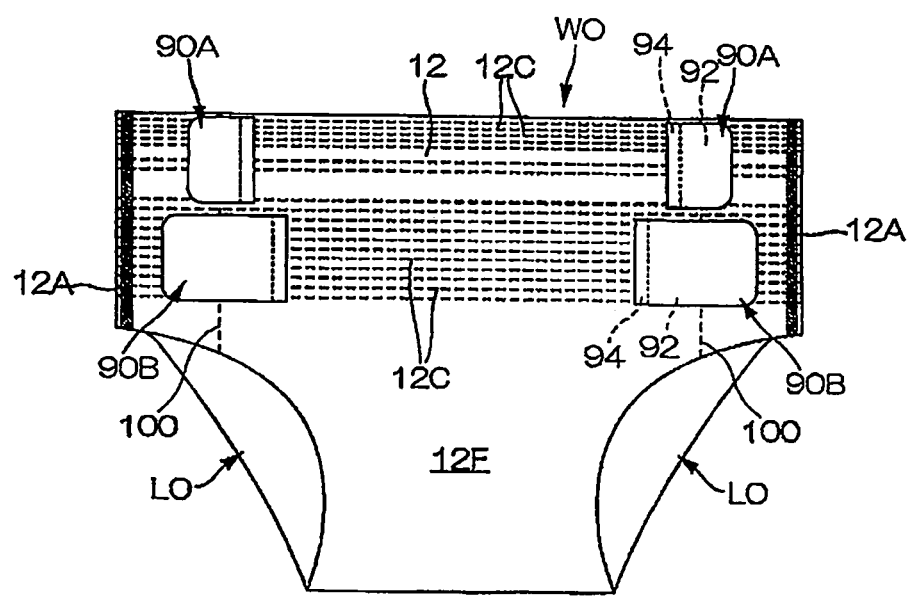
FIG. 11 is a front view of the fifth embodiment as a tape-fastening type.

In providing a plurality of fastening tapes on each of the both side portions, the fastening tapes 90 may be separate parts in advance, or may be divided into a plurality of parts 90A and 90B by tearing the diaper along the perforated lines 93, as FIG. 10 shows a diaper in a final product state and FIG. 11 shows a diaper as a tape-fastened type. In the latter case, a plurality of hook members 92 are arranged in the fastening tape 90 in the longitudinal direction at a predetermined spacing therebetween, and the perforated line 93 is provided in a section between the hook members 92, whereby pickup portions 94 without the hook members 92 can be formed at the separated parts 90A and 90B.

Sixth Embodiment

Figure 12:
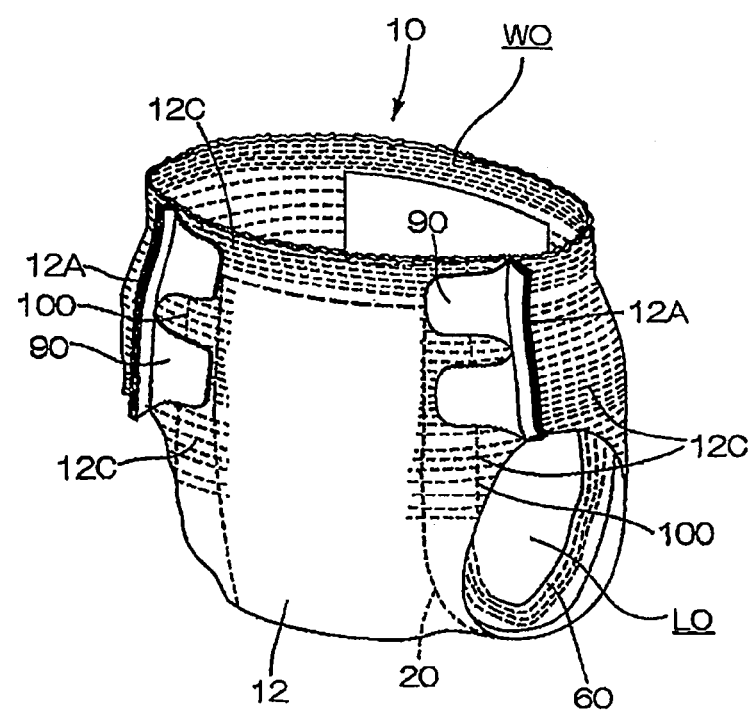
FIG. 12 is a perspective view of a sixth embodiment.
Figure 13:
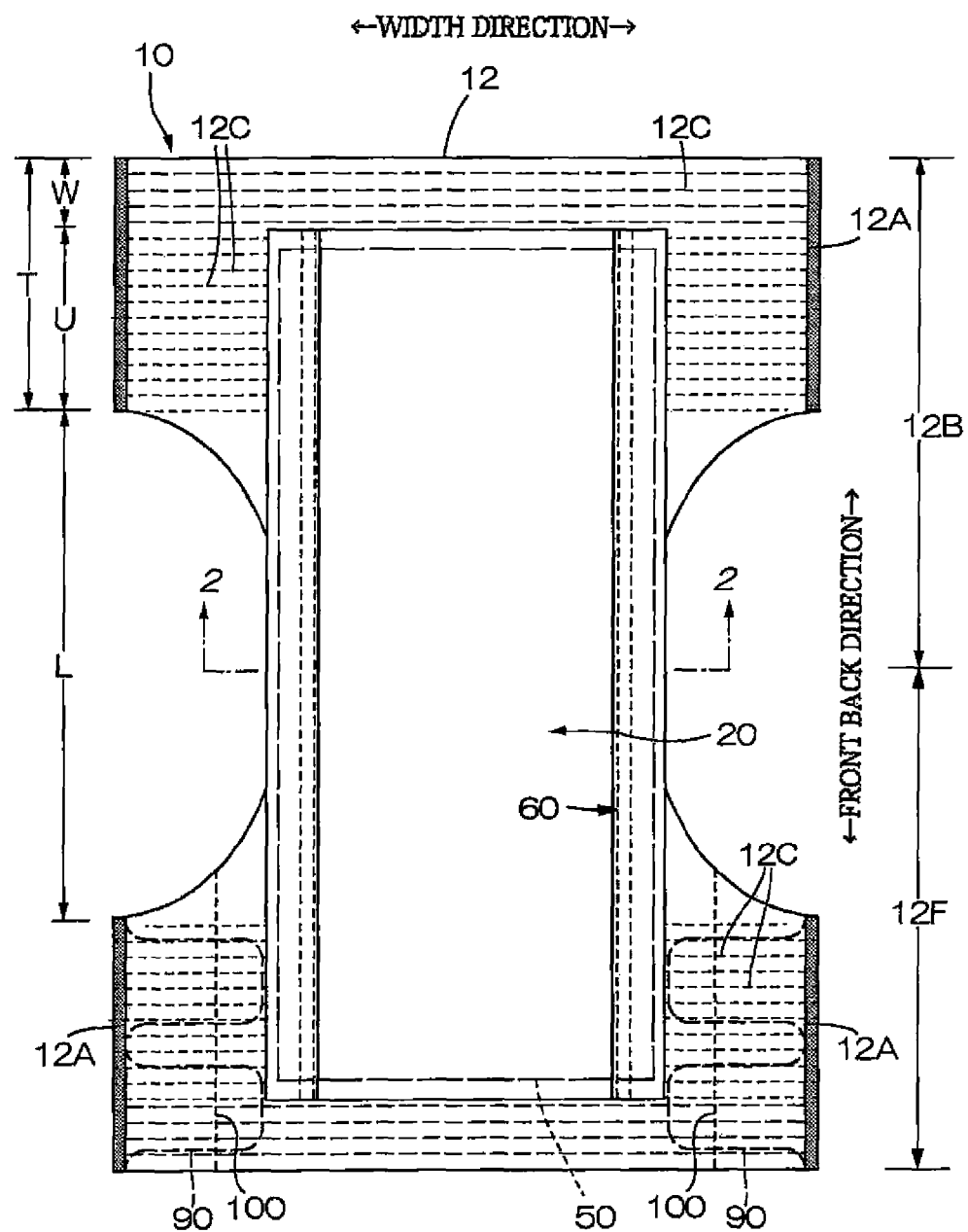
FIG. 13 is a developed view of the sixth embodiment.

As shown in FIGS. 12 and 13, the fastening tapes 90 can be fixed to the joined portions on the both side portions of the diaper. In the illustrated example, a plurality of fastening tapes 90, 90 are arranged in the front body part 12F so as to cover the virtually entire around-waist portion T on the both side portions in the front-back direction, and are not provided in the back body part 12B. Although not shown, the fastening tapes 90 may also be arranged only in the back body part 12B depending on formed positions of the perforated lines 100, and this arrangement will not be described because it is the same as the foregoing arrangement except that the front body part is replaced by the back body part. In addition, depending on the formed positions of the perforated lines 100, the single fastening tape 90 may be provided on each of the both side portions or may be provided only at an upper or lower portion in the vertical direction.

Figure 14:
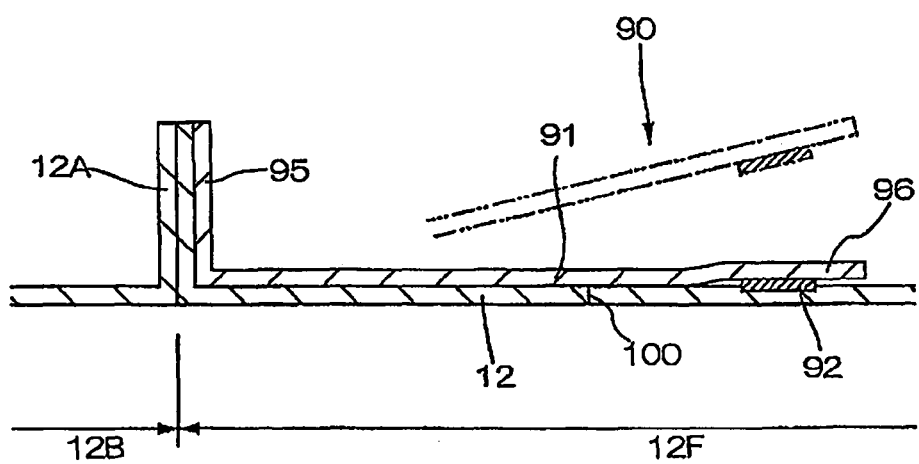
FIG. 14 is a transverse cross-sectional view of a fastening tape portion of the sixth embodiment.

The illustrated fastening tape 90 is a belt-shaped member extending in the width direction, and a base end portion 95 is fixed only to the joined portion 12A as shown in detail in FIG. 14. This fixation may also be near the joined portion 12A (on the side close to the middle area in the width direction). The base end portion 95 of the fastening tape 90 may be fixed with a hot-melt adhesive, but is preferably fixed by heat sealing in formation of the joined portion 12A. In this case, the base end portion 95 of the fastening tape 90 is increased in strength, and thus becomes less prone to come off even if a high load is applied around the waist due to the wearer's strenuous movement. In addition, the fastening tape 90 can be fixed concurrently with formation of the joined portion 12A, which results in higher processing efficiency.

A portion 96 of the fastening tape 90 at a leading end of the base end portion 95 is freely movable with respect to the base end portion 95, and includes a hook member 92 that can be engaged on the external surface of the diaper.

Figure 18:
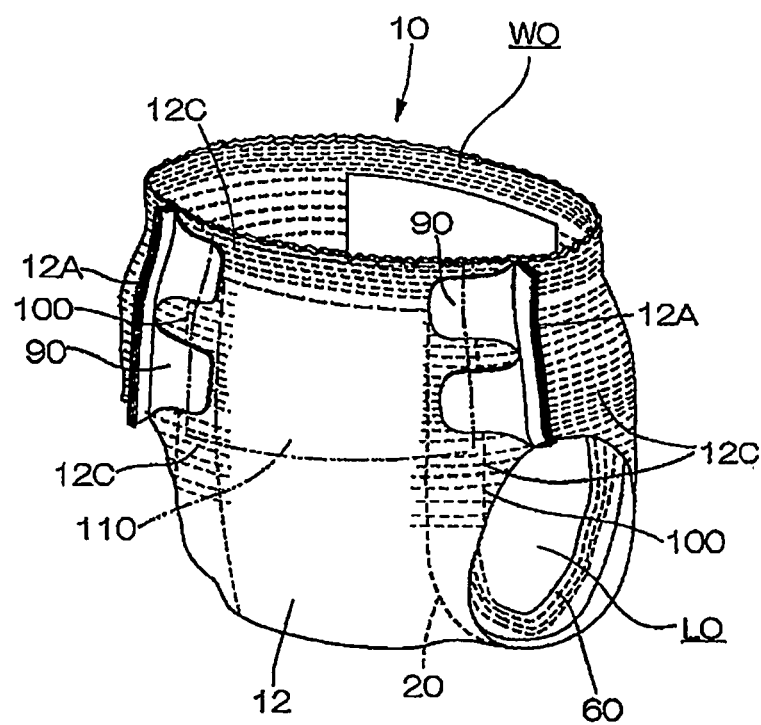
FIG. 18 is a perspective view of another embodiment.

If the external surface of the outer sheet 12 is formed by a nonwoven fabric, the hook member 92 can use a hook member of a mechanical fastener so that the hooks are entangled in fibers of the nonwoven fabric for engagement. If necessary, for example, if the engagement may become insufficient, a loop member having loops for entanglement with the hooks of a mechanical fastener, or a target tape 110 such as a resin tape to which an adhesive material favorably adheres, may be provided at an appropriate places between the fastening tapes 90, 90, as shown in FIG. 18.

The leading end portion 96 of the fastening tape 90 can be configured as to extend sufficiently in use, by folding in advance a plurality of times and temporarily fixing, or with the use of a resilient and elastic material such as natural rubber or synthetic rubber.

Meanwhile, in this embodiment, rather than simply providing the fastening tapes 90, it is preferred that a tensile stress on a body part with the fastening tapes 90 (the front body part 12F) on elastically deforming in the width direction is larger than a tensile stress on a body part without the fastening tapes 90 (the back body part 12B) on elastically deforming in the width direction. Such a difference in tensile stress on elastically deforming in the width direction can be achieved by making the resilient and elastic members 12C in the body parts 12F and 12B vary in elastic force (kind of a material), number, thickness, and location, as appropriate.

Preferably, a tensile stress on the front body part 12F on elastically deforming in the width direction is larger by 10% or more than a tensile stress on the back body part 12B on elastically deforming in the width direction, although it is not always defined so. Within a range of elastic deforming in use, if a difference in tensile stress is too large, a body part without the fastening tapes 90 (the back body part 12B in the illustrated embodiment) is excessively extended and thus provides an insufficient fit to the body of a wearer, whereas if a difference in tensile stress is too small, a body part with the fastening tapes 90 (the front body part 12F in the illustrated embodiment) is decreased in displacement on the both side portions.

Figure 16:
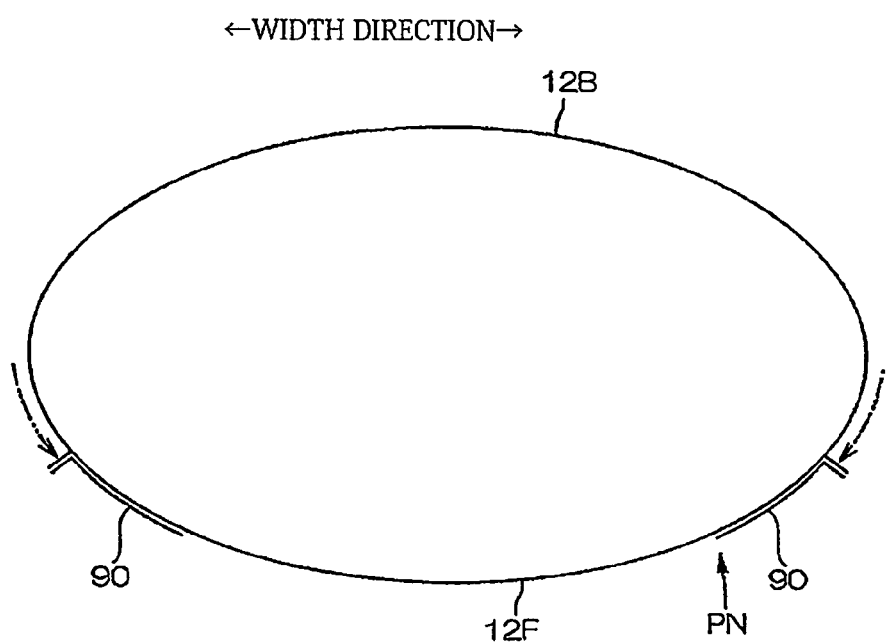
FIG. 16 is a schematic plan view for describing functions of the sixth embodiment.

FIG. 16 is a schematic plan view of a diaper PN in this embodiment where the front body part 12F with the fastening tapes 90 is contracted and the back body part 12B without the fastening tapes 90 is extended due to a difference in tensile stress on elastically deforming, and the both side portions of the front body part 12F with the fastening tapes 90 are located together with the fastening tapes 90 closer to the middle area of the diaper in the width direction, as shown by arrows of chain double-dashed lines in the diagram. Accordingly, it is possible to adjust the width of the diaper in a balanced manner even if a wearer lies on his/her side as stated above. In addition, the fastening tapes 90 may be fixed to the joined portions 12A so that the fastening tapes 90 are located closer to the middle area in the width direction and thus becomes easy to pick up. Width adjustment is made by picking up the fastening tapes 90 in the diaper attached to the body of a wearer, and engaging the hook members 92 of the fastening tapes 90 in the external surface of the front body part 12F at appropriate places closer to the middle area in the width direction, while adjusting a degree of tightness of the diaper around the waist of the wearer.

In addition, if the continuous perforated lines 100 are formed in the front-back direction from the waist opening WO to the leg openings LO in the sixth embodiment, the perforated lines 100 are preferably located between the fastening tapes 90, 90 in the body part with the fastening tapes 90 (the front body part 12F) so as to pass between the engagement positions of the hook members 92 (the engagement positions in adjusting the diaper width) and the base end portions 95 of the fastening tapes 90, as illustrated in the diagram. The perforated lines 100 can be appropriately formed in a dogleg-like flexion line, wavy line, or others as far as it extends longitudinally.

Figure 15:
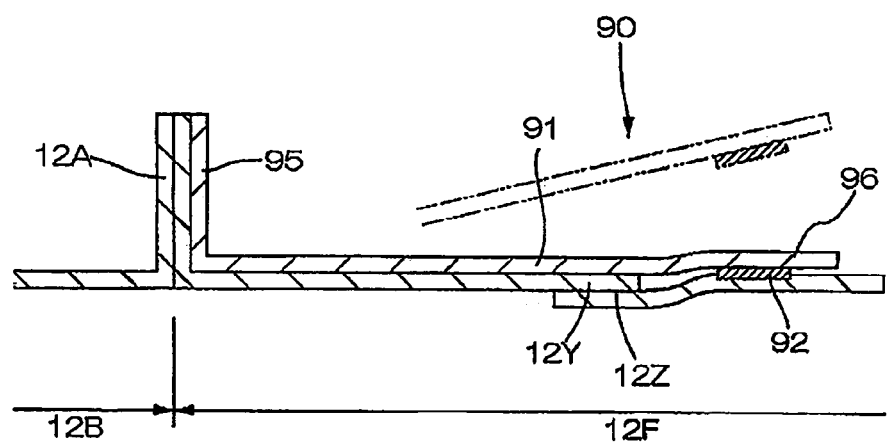
FIG. 15 is a transverse cross-sectional view of the fastening tape portion of the sixth embodiment.

With these perforated lines 100, it is possible to shorten the diaper width significantly without impairing a fit to the body of a wearer by tearing the diaper along the perforated lines 100 on the both side portions of the diaper as required, and placing a portion 12Y on one side of each torn section over a portion 12Z on the other side of the torn section as shown in FIG. 15. In addition, the diaper can be used as a tape-fastening type by tearing along the perforated lines 100 as stated above. In the illustrated example, the portion 12Z on the side closer to the middle area in the width direction with respect to the perforated line 100 is located inside and the portion 21Y on the side with the fastening tape 90 is located outside, but these portions may be located in a reversed manner.

The perforated lines 100 are preferably arranged between the hook members 92 and the base end portions 95, or so as to overlap the hook members 92 in a product state. This prevents the diaper from being unintentionally torn along the perforated lines 100 when the diaper is unused or used as an underpants type.

Figure 17:
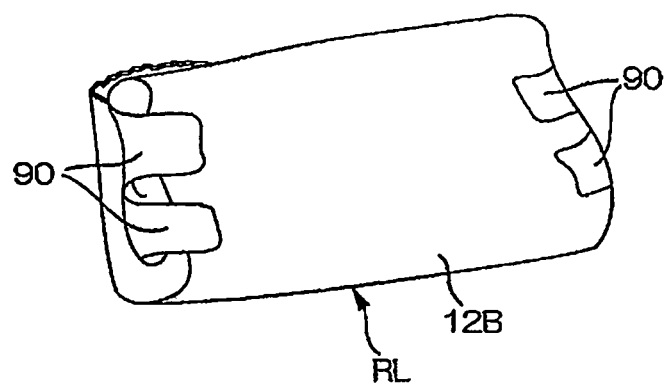
FIG. 17 is a perspective view showing schematically a procedure for disposal of a diaper.

Meanwhile, in disposal of a used diaper as shown in FIG. 17, the diaper can be fixedly rolled up without soiling, by curling up the crotch L toward the front body part F, turning the fastening tapes 90, 90 on the both sides of the front body part 12F to the external surface of a curling portion RL, and engaging the hook members 92 in the external surface of the curling portion RL. By using the fastening tapes 90 both for adjustment of tightness around the waist of a wearer and for disposal of a used diaper as stated above, it is possible to reduce material costs significantly as compared with the case of providing individually separate components for the above purposes.

Other Embodiments (a) The fastening tapes 90 are preferably provided with pictures of a cartoon character or the like so as to be visible from the external surfaces. By printing such pictures on the fastening tapes 90 that can be fully separated from the external surface of the diaper, the fastening tapes 90 can be fastened to clothes or the like or can be used as emblem-like articles giving pleasure of collection.

(b) The absorbent main unit 20 is preferably provided with an indication means for indicating voiding of urine. Such an indication means can be formed by coating the inner surface of the liquid impervious sheet 70 (the absorbent element 50—side surface) with a composition changing color when exposed to liquid, for example.

(c) Although the perforated lines 100 are provided on the both side portions of the front body part 12F in the foregoing embodiments, similar perforated lines may be provided on the both side portions of the back body part 12B instead.

(d) The fastening tapes 90 may be fastened in the final product at places other than the perforated lines 100.

(e) Although the engagement sections of the fastening tapes 90 use the hook members 92 in the foregoing embodiments, there is no particular limitation on a material for the engagement sections as far as the material can be engaged on the external surface of the diaper, and the hook members 92 may be replaced by some adhesive material layers, for example. In addition, although a nonwoven fabric of the external surface of the diaper is used for engagement of the fastening tapes 90 in the foregoing embodiments, if necessary, e.g., if the engagement may become insufficient, it is possible to provide a target tape having loops for entanglement with the hook member 92, or a resin tape to which an adhesive material favorably adheres, to the external surface of the diaper in whole or part.

(f) At least part of the fastening tape 90 may be elastically resilient. This provides an increased fit and further widens a degree of freedom for size adjustment. In particular, if a plurality of hook members 92 are arranged with a predetermined spacing therebetween as in the fourth embodiment, the hook members 92 are configured in such a manner that at least part of an area between the hook members 92 is elastically resilient. In using the diaper as a tape-fastening type, the hook members 92 of the fastening tapes 90 may be engaged on the ventral and back parts separated along the perforated lines 100 to join the ventral and back parts, thereby achieving a larger maximum size of the waist line as compared with the case of using the diaper as an underpants type.

In making the fastening tape 90 elastically resilient as stated above, at least part of the fastening tape 90 (at least either the base material sheet 91 or the hook member 92) may be formed by a resilient and elastic material such as a rubber sheet, or by a combination of a resilient and elastic material and a non-resilient material such as an elastic sheet in which a sheet-like or thread-like elastic material is attached to a nonwoven fabric sheet or the like in the extended state. In addition, such a resilient and elastic material may be partly subjected to a non-resilient treatment, or in reverse, such a non-resilient material may be subjected to a resilient-and-elastic treatment. Further, the fastening tape 90 may be entirely resilient, or may be configured such that the engagement section, the pickup portion, and the base end portion are not resilient.

INDUSTRIAL APPLICABILITY

The present invention applies to underpants type disposable diapers.

The invention claimed is:

1. An underpants type disposable diaper, comprising: a front body part and a back body part which are jointed to each other at both side portions thereof to thereby form joined portions on both sides, a waist opening, and a pair of right and left leg openings;
   an absorbent main unit which is a portion that receives, absorbs and retains excreted objects and extends to a crotch and portions on both front and back sides of the crotch; and
   a plurality of elongated resilient and elastic members which are fixed anywhere in an area from the waist opening to the leg openings of the front and back parts and a lengthwise direction of said resilient and elastic members extends in a width direction of the diaper, and wherein
   perforated lines are formed in the front body part or back body part so as to extend from an edge of the waist opening to edges of the leg openings, said perforated lines being provided in width direction positions that are separated so as to be closer to a middle area in a width direction than said joined portions and are separated so as to be closer to an outward area in a width direction than said absorbent main unit,
   the resilient and elastic members are arranged on both sides of the perforated lines such that ends thereof facing to the perforated lines are placed at the same positions as the perforated lines or near the perforated lines,
   at least one pair of right and left fastening tapes each having only one engagement section that is provided on an inner surface thereof and straddles one of the perforated lines, said fastening tapes being provided within width direction ranges that are separated so as to be closer to said middle area in said width direction than said joined portions and separated so as to be closer to said outward areas in said width direction than said absorbent main unit, and
   each one of the at least one pair of fastening tapes is detachably engaged on an external surface of the diaper by the engagement section that straddles both sides of one of the perforated lines, and said tape is completely separated, for its entirety, from the external surface of the diaper by releasing the engagement of the engagement sections.

2. The underpants type disposable diaper according to claim 1, wherein the resilient and elastic member is fixed so as to cross the perforated line in an extended state in a direction of crossing, and then cut at the same position as the perforated line or near the perforated line.

3. The underpants type disposable diaper according to claim 2, wherein
   the elongated resilient and elastic member is fixed only at a portion that overlaps the engagement section of the fastening tape and a portion near the overlapping portion, in an extended state in a direction that crosses the perforated line.

4. The underpants type disposable diaper according to claim 2 or 3, wherein, when the front and back body parts are under elastic deformation in the width direction, a tensile stress on one body part with the fastening tapes is larger than a tensile stress on the other body part without the fastening tapes.

5. The underpants type disposable diaper according to claim 4, wherein the plurality of fastening tapes are provided on each of the both side portions of the front body part or back body part.

6. An underpants type disposable diaper comprising:
a front body part and a back body part which are jointed to each other at both side portions thereof to thereby form joined portions on both sides, a waist opening, and a pair of right and left leg openings; and
a plurality of elongated resilient and elastic members which are fixed anywhere in an area from the waist opening to the leg openings of the front and back parts and a lengthwise direction of said resilient and elastic members extends in a width direction of the diaper, and wherein
perforated lines are formed on the both side portions of the front body part or back body part so as to extend from an edge of the waist opening to edges of the leg openings,
the resilient and elastic members are arranged on both sides of the perforated lines such that ends thereof facing to the perforated lines are placed at the same positions as the perforated lines or near the perforated lines,
a fastening tape having an engagement section that is provided on an inner surface thereof and straddles the perforated line,
said fastening tape is detachably engaged on an external surface of the diaper by the engagement section and said fastening tape is completely separated, for its entirety, from the external surface of the diaper by releasing engagement of the engagement sections,
a plurality of the engagement sections are arranged with a predetermined spacing therebetween on the inner surface of the fastening tape, and
the fastening tape is elastically resilient at at least a portion of each area between the engagement sections.

7. An underpants type disposable diaper comprising:
a front body part and a back body part which are jointed to each other at both side portions thereof to thereby form joined portions on both sides, a waist opening, and a pair of right and left leg openings; and
a plurality of elongated resilient and elastic members which are fixed anywhere in an area from the waist opening to the leg openings of the front and back parts and a lengthwise direction of said resilient and elastic members extends in a width direction of the diaper, and wherein
perforated lines are formed on the both side portions of the front body part or back body part so as to extend from an edge of the waist opening to edges of the leg openings,
the resilient and elastic members are arranged on both sides of the perforated lines such that ends thereof facing to the perforated lines are placed at the same positions as the perforated lines or near the perforated lines,
a fastening tape having an engagement section that is provided on an inner surface thereof and straddles the perforated line,
a plurality of the engagement sections are arranged with a predetermined spacing therebetween on the inner surface of the fastening tape,
said fastening tape is detachably engaged on an external surface of the diaper by the engagement sections and said tape is completely separated, for its entirety, from the external surface of the diaper by releasing engagement of the engagement sections, and
the fastening tape has at least one perforated line between two engagement sections provided thereon and can be completely separated into a plurality of fastening tapes by tearing along the perforated line.

* * * * *